United States Patent [19]
Kropf et al.

[11] Patent Number: 5,387,214
[45] Date of Patent: Feb. 7, 1995

[54] BOLT FOR BEING DRIVEN INTO BONE TISSUE

[76] Inventors: Philipp R. Kropf, Chliwisstrasse 21, CH-8142 Uitikon; Albert Geisser, Stationsstrasse 33, CH-6373 Ennetbürgen, both of Switzerland

[21] Appl. No.: 119,612

[22] Filed: Sep. 10, 1993

[30] Foreign Application Priority Data

Sep. 23, 1992 [CH] Switzerland ............ 2971/92

[51] Int. Cl.⁶ .................................. A61B 17/58
[52] U.S. Cl. .................................... 606/64
[58] Field of Search ............... 606/62, 63, 64, 67, 606/68, 69, 60, 72, 75

[56] References Cited

U.S. PATENT DOCUMENTS

| | | | |
|---|---|---|---|
| 2,490,364 | 12/1949 | Livingston | 606/68 |
| 2,627,855 | 2/1953 | Price | 606/67 |
| 3,334,624 | 8/1967 | Schneider et al. | 606/62 |
| 3,741,205 | 6/1973 | Markolf . | |
| 3,791,380 | 2/1974 | Dawidowski | 606/68 |
| 4,103,683 | 8/1978 | Neufeld | 606/96 |
| 5,057,103 | 10/1991 | Davis | 606/68 X |
| 5,085,660 | 2/1992 | Lin | 606/69 |
| 5,147,361 | 9/1992 | Ojima et al. | 606/69 |

FOREIGN PATENT DOCUMENTS

| | | |
|---|---|---|
| 384359 | 12/1981 | Austria . |
| 948690 | 7/1947 | France . |
| 3138311 | 9/1980 | Germany . |
| 3933217 | 10/1989 | Germany . |
| 669724 | 4/1986 | Switzerland . |
| 670754 | 9/1986 | Switzerland . |

*Primary Examiner*—Tamara L. Graysay
*Attorney, Agent, or Firm*—Gordon W. Hueschen

[57] ABSTRACT

A combination of bone-fixing elements comprising an intramedullary nail having an aperture therein and a cooperating locking bolt, the locking bolt having a shank for extending into the aperture in the intramedullary nail, the locking bolt comprising a pin for enlarging a diameter of at least a part of the shank when the shank is present in the aperture, or the nail and the bolt comprising surfaces for preventing rotation of the bolt in the nail, in either case thereby to lock the bolt in the intramedullary nail and to lock the intramedullary nail in place in a bone when located therein.

11 Claims, 4 Drawing Sheets

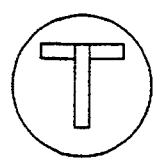 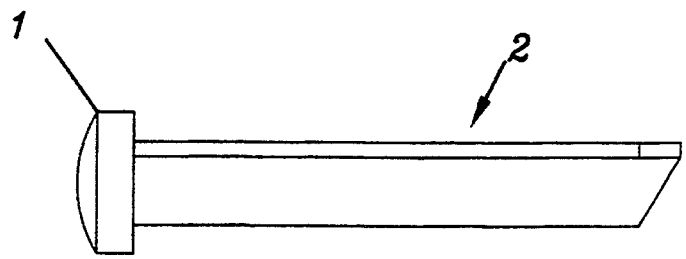
*FIG. 1b*  *FIG. 1a*
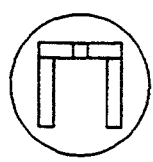 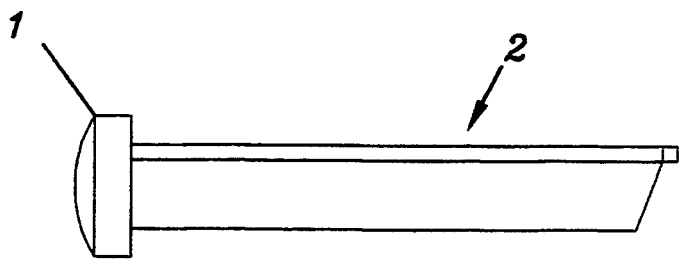
*FIG. 1d*  *FIG. 1c*
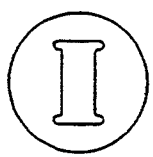 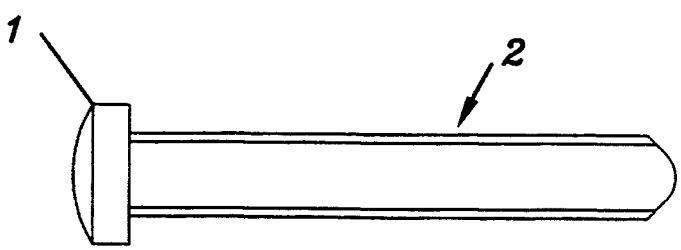
*FIG. 1f*  *FIG. 1e*
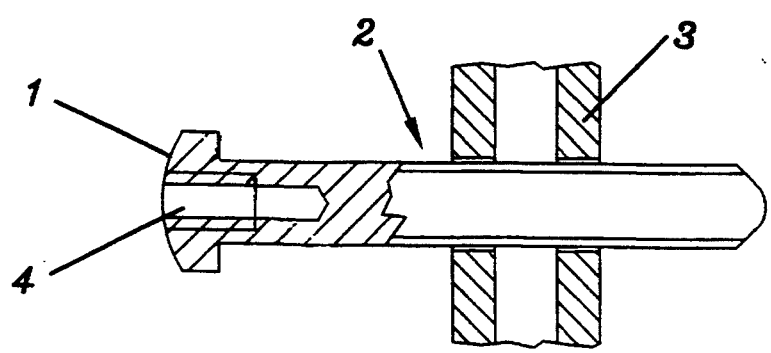
*FIG. 2*

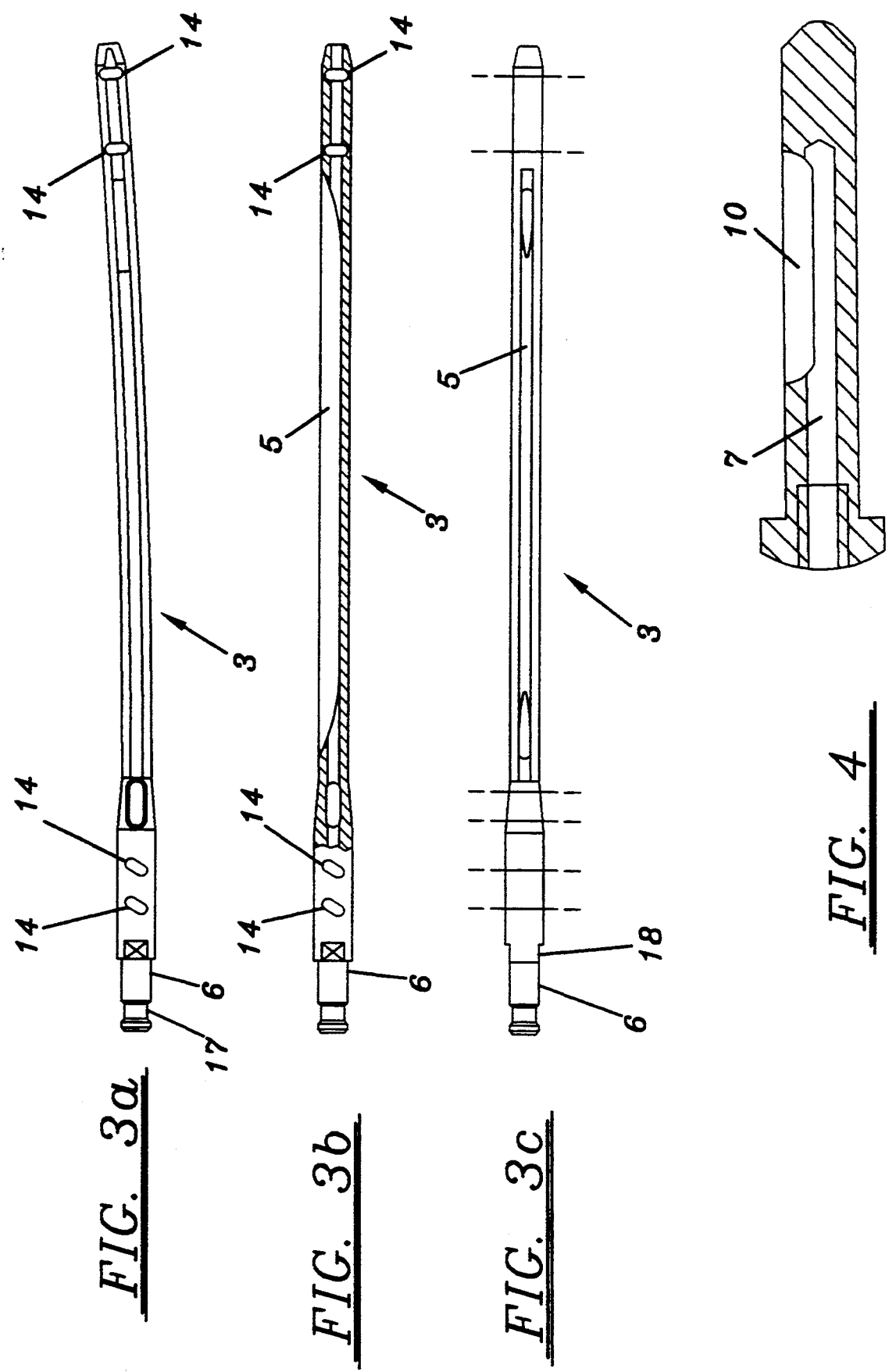

BOLT FOR BEING DRIVEN INTO BONE TISSUE

BACKGROUND OF THE INVENTION

1. FIELD OF THE INVENTION

The invention relates to a bolt for being driven into bone tissue and an intramedullary nail locked in a bone with such a bolt.

2. DESCRIPTION OF THE PRIOR ART

Stabilizing aids, plates for osteosynthesis, prostheses for joints, intramedullary nails, etc. are usually fixed to the bone by means of screws or profiled nails. Typical screws and nails of this kind are described in CH 670 754 and CH 669 724.

These conventional screws and nails are provided with a threading, barb-like ridges, or similar irregularities extending over at least part of their shank for preventing the bolts from slipping out of the bone. They have therefore an irregular surface, which can lead to manyfold problems. If such screws or nails are e.g. subjected to static or dynamic stress, they cause an inhomogeneous distribution of pressure in the bone tissue. High peak pressures are e.g. found at the edge of a threading or a ridge. Such high pressure can cause a resorption of bone tissue and thereby weaken the bone and loosen the screw or nail, respectively. This can lead to an undesired distribution of forces in the bone and a fracturing of bone, screw, or nail.

If a screw is e.g. driven through a tubular bone and screwed with its tip into the hard bone tissue lying opposite its head, the described effect can lead to a loosening of the screwed tip and a redistribution of forces towards the head of the screw and, resulting in breaking of the screw or damaging of the bone tissue at the head of the screw.

Furthermore, conventional screws are not rotationally stable, i.e. they can be rotated and thereby loosened, which again leads to additional forces and an inhomogeneous distribution of pressure and can therefore damage the screw or the bone.

Furthermore, most conventional solutions require that holes are drilled into the bone or even that a threading must be cut in the bone tissue prior to inserting the screw or nail. This leads to an additional working step. It also causes a loss of bone material and thereby a further weakening of the bone.

SUMMARY OF THE INVENTION

Therefore it is an object of the invention to provide an element that can be used as a locking or fixing element in a bone and that does not show the disadvantages mentioned above.

Now, in order to implement these and still further objects of the invention, which will become more readily apparent as the description proceeds, the inventive bolt or pin is characterized by the features that it comprises a head and a shank, wherein said shank has a substantially smooth surface.

Since the surface of the shank or shaft is substantially smooth and comprises no threading, sharp ridges, barbs, or the like, it does not generate an inhomogeneous pressure distribution in the bone tissue. This prevents a resorption of bone material.

Furthermore, the bolt can be driven directly into the solid bone. It is not necessary to drill a hole into the bone before introducing the bolt. This leads to a considerable decrease in operation time and a reduction in the loss of bone tissue.

The inventive bolt is especially suited for being driven into the bone by an oscillatory, pneumatic percussion tool. By using such a tool, the strain on the bone and the danger of creating cracks in the bone are very small. Bolts inserted in this way are held very securely in the bone tissue.

In a preferred embodiment of the invention, the bolt is secured against a rotation by having a cross section that is not rotationally symmetric.

BRIEF DESCRIPTION OF THE DRAWINGS

The invention will be better understood and objects other than those set forth above will become apparent when consideration is given to the following detailed description thereof. Such description makes reference to the annexed drawings, wherein:

FIGS. 1a, 1c, and 1e show lateral and FIGS. 1b, 1d, and 1f show front or end views of three different embodiments of the bolt with differing shank cross sections;

FIG. 2 shows a bolt inserted in an intramedullary nail;

FIGS. 3a, 3b, and 3c respectively show lateral views of a bent intramedullary nail, and a cross sectional view and a top view of an intramedullary nail with fixing apertures shaped to receive the inventive bolts;

FIG. 4 shows a bolt with a shank that can be expanded after insertion into the bone;

FIG.

Figure 6A:
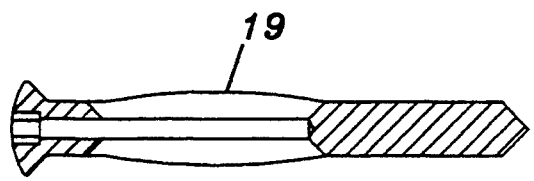
Figure 6B:
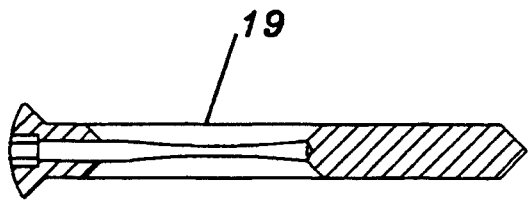
Figure 6C:
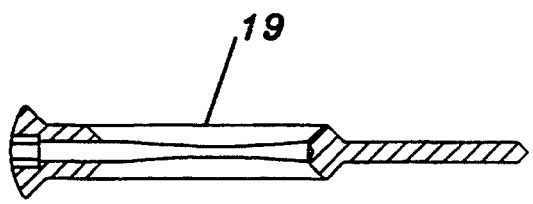

FIGS. 6a, 6b, and 6c respectively show another embodiment of a bolt with an expandable shank in its expanded state (6a) and in its non-expanded state (6b), the bolt in 6a and 6b having a substantially constant diameter over its entire shank, including the forward portion of the shank except the expandable portion of the shank. FIG. 6c shows the same type of bolt but having a reduced diameter over a portion of the shank. a second embodiment of a bolt with an expandable shank in its expanded state (6a) and in its nonexpanded (6b) state; the outer set of broken lines indicating a bolt having a substantially constant diameter over its entire shank, including the forward portion of the shank except the expandable portion of the shank, whereas the inner set of broken lines indicate a bolt having a reduced diameter over this portion of the shank.

Figures 8A, 8C:
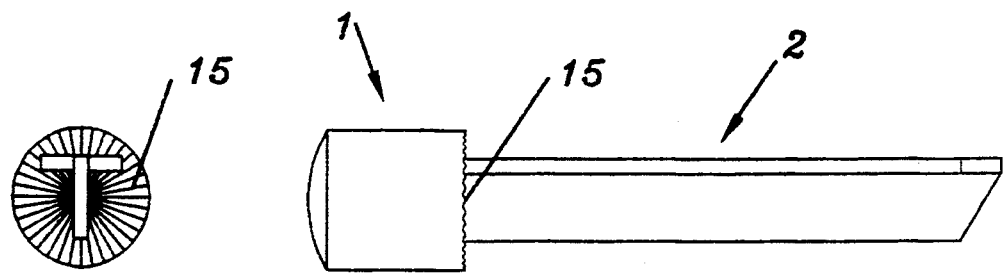
Figure 8B:
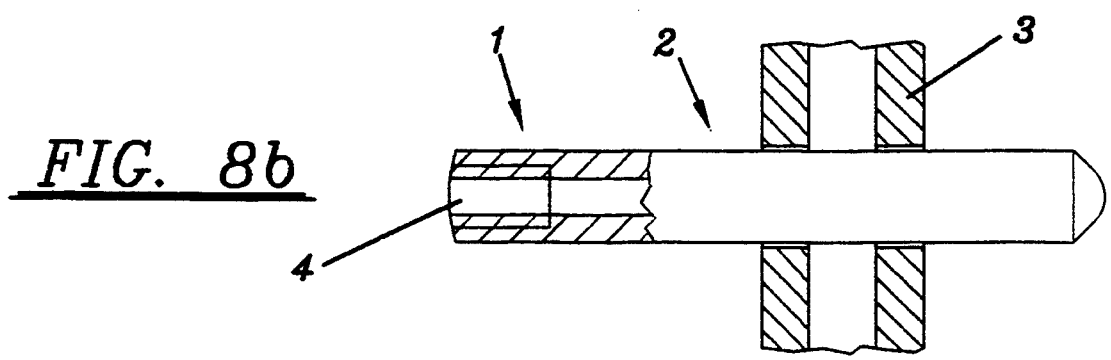
Figures 9A, 9B:
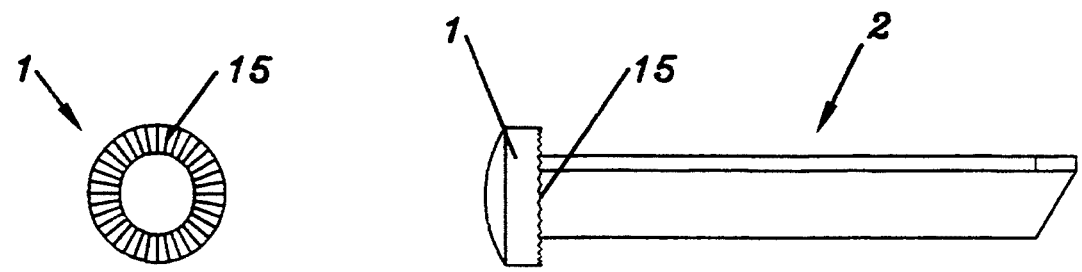
Figures 10A, 10B:
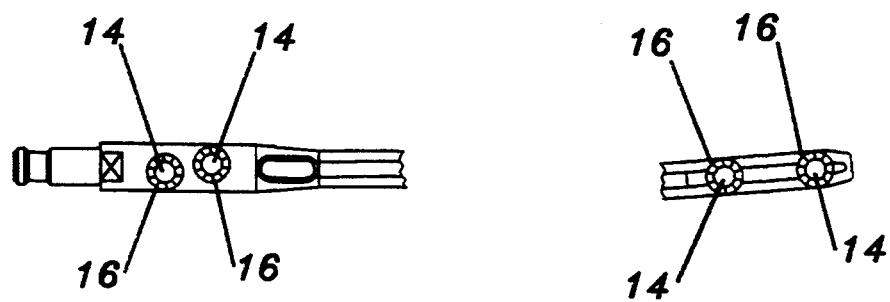

FIGS. 7a through 7d show further embodiments of the inventive bolt;

FIGS. 8a and 8b show two bolts with differing heads; FIG. 8c showing an end view of the bolt of FIG. 8a, having an interlocking profile on the bottom surface of its head;

FIG. 9a shows an embodiment of the bolt with an interlocking profile on the bottom surface of its head, and FIG. 9b shows an end view of said bolt and said bottom surface; and FIGS. 10a and 10b show intramedullary nails suitable for receiving the bolt of FIG. 9.

DESCRIPTION OF THE PREFERRED EMBODIMENTS

Three preferred embodiments of the inventive bolt or pin are shown in FIGS. 1 through 1f. In each of these embodiments, the bolt is provided with a head 1 and a shank or shaft 2. Along its longitudinal direction, the shank is essentially smooth and tapered or tipped at its forward end. As it can be seen from FIGS. 1a–1f, the cross section of the shank can be of various shape. It can e.g. be U-, I-, T-, lens- or ellipse-shaped. In a further embodiment as described below, it can also be round.

The surface of the shank is substantially smooth, i.e. it does not have a threading, barb-like ridges or other macroscopic irregularities. Smaller irregularities in a microscopic scale (up to the range of several 100 μm) are, however, possible. The shank can e.g. be slightly roughened for better contact with the bone tissue.

Because its shank does not have rotational symmetry, a bolt as shown in FIGS. 1a–1f is rotationally stable and cannot be loosened by turning. This improves the hold of the bolt in the bone. Furthermore, the increase of shank surface, which is especially pronounced in the embodiments according to FIGS. 1a and 1c, allows an even more intimate contact between the shank and the bone tissue.

Because the shank of the inventive bolt is substantially smooth in its longitudinal direction, it is especially suited for being driven into solid bone. In contrary to conventional screws it is not screwed helically into the bone tissue but driven into it by means of a force acting along its longitudinal axis.

The shank 2 is preferably tapered. In the shown preferred embodiments of FIGS. 1a, c and e, the diameter of the shank remains constant or decreases with increasing distance from the head 1. This facilitates driving the bolt into the bone.

As it has been mentioned above, an advantage of the smooth shank lies in the fact that it does not generate pressure peaks in the bone tissue and distributes the pressure evenly. This avoids a resorption of bone tissue and stimulates its growth.

It is principally possible to drive the bolt into the bone by using a conventional hammer, sliding hammer, etc. The strong individual pulses generated by such a tool can, however, burst a weak bone if the bone has not been provided with a bore to receive the bolt. Much better results can be achieved by using an oscillatory, pneumatic percussion tool such as described in the European patent application EP 452 543. Such tool is especially suited for driving the inventive bolt into the bone because its high frequency pulses have a much smaller amplitude than those generated by a conventional hammer or sliding hammer.

In this way it is easily possible to drive a bolt directly into the non-prepared, solid bone. It is not necessary to drill a hole or aperture to receive the bolt. This simplifies the operation procedure considerably.

Furthermore, it is possible to store the bolts in a magazine mounted to the percussion tool, from where they can be automatically fed to the tool.

FIG. 2 shows a further embodiment of the bolt. This bolt is inserted in an element 3. This element 3 can e.g. be an apertured intramedullary nail lying in the bone and being locked or fixed by the shaft or shank 2 of the bolt.

The head 1 of this bolt is provided with a recess 4. This recess is adapted to the tool used for driving the bolt into the bone. It can e.g. be shaped to receive a hexagon bar or have an internal thread to receive a screw.

The inventive bolt can e.g. be used to fix individual fragments of bone. It is, however, also suited for holding or locking plates for osteosynthesis, intramedullary nails or prostheses. These elements must be provided with openings or apertures for receiving the bolts, which openings are preferably shaped to match the cross section of the bolt. An intramedullary nail of this kind is shown in FIG. 3. It comprises holes or apertures 14 for receiving the shank of the bolt. The holes or apertures 14 are oblong and suited for receiving the bolt of FIGS. 1e and 1f.

Similarly, e.g. osteosynthesis plates can be provided with suitably shaped holes or apertures.

The intramedullary nail of FIGS. 3a–3c is formed to be manipulated by an oscillatory pneumatic percussion tool such as described above. Using such a tool, it can be driven directly into the bone. For this purpose, the nail is provided with a macroscopically substantially smooth surface and a drain 5 for draining medullary material when being driven into the bone. The drain 5 comprises a longitudinal notch with drainage canals. The head 6 of the nail is formed to provide a connection to the percussion tool that transfers pulling, pushing and rotating forces. Therefore, the head 6 has a circumferential groove 17 to be engaged by the tool. Furthermore, two opposite, flat faces 18 are provided, which can abut on corresponding surfaces of the tool for preventing a rotation between the tool and the nail.

In this way it is possible to provide a stiff connection between the percussion tool and the nail. This allows an optimum control of the nail's position while it is driven into the bone.

By using the described pneumatic percussion tool, a damage of the bone can be avoided, even if the nail has a comparatively large diameter. Therefore it is possible to use a nail that snugly contacts the hard bone.

Since it is impossible to position an intramedullary nail and its fixing bolts or screws with very high accuracy, the fixing holes or apertures 14 of the nail must be chosen somewhat larger than the diameters of the fixing bolts. This allows to correct for positioning errors of the components but results in loose connections between bolts and nail.

Figure 5:
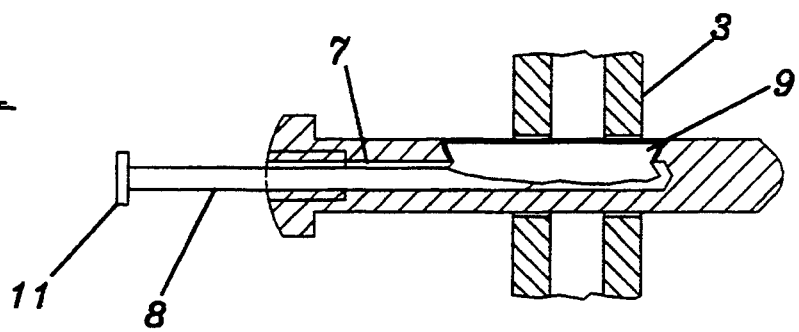
FIG. 5 shows the bolt of FIG. 4 with inserted jamming member.

This problem can be avoided by using a bolt as shown in FIGS. 4 and 5. This bolt is provided with a longitudinal bore or cavity 7 for receiving a pin 8. Furthermore, part of the shank wall is replaced by a jamming member 9 lying in the lateral opening 10. The jamming member 9 is formed to extend into the central cavity 7. It is only loosely or elastically connected to the bolt. When the pin 8 is brought into the cavity 7, it pushes the jamming element 9 outward.

When driving the bolt into the bone, the pin 8 is not inserted, the jamming element 9 lies at its innermost position, and the surface of the shank is even. The bolt can therefore be driven into the bone like any of the bolts shown in FIGS. 1a, 1c, and 1e. The position of the jamming element 9 is chosen such that, once the bolt is in its final position, the jamming element is located in the intramedullary nail 3. Now the pin 8 is driven into the cavity 7, whereupon the jamming element 9 is pressed against the nail 3 and provides a tight fit of the bolt in the nail. The pin 8 can e.g. be driven into the cavity by using an oscillatory pneumatic percussion tool as described above.

For removing the bolt, the pin 8 must first be pulled out. This can e.g. be done by using a suitable pair of tongues adapted to grip the head 11 of the pin. By removing the pin 8 from the cavity, the jamming element 9 releases the nail 3.

FIGS. 6a and 6b show an alternative embodiment of a bolt with an expandable shank. FIG. 6a shows the shank in its expanded state, FIG. 6b in its non-expanded state. Similar to the bolt shown in FIGS. 4 and 5, this bolt also has a longitudinal bore or cavity. In a section of the shank, the diameter of the cavity is smaller than the diameter of the pin to be inserted into it (cf. FIG. 6b). Furthermore, the expandable section of the shank can be provided with a plurality of longitudinal slots 19. When the pin is driven into this bolt, it will push the thickened shank walls outwardly. This movement is facilitated by the longitudinal slots 19. In this way it is again possible to expand the shank diameter by driving the pin into a longitudinal cavity of the bolt.

In fabrication, this bolt can first be formed with a thickened shank and the slots 19. In a next step the bolt is provided with a central bore. Then the shank is radially compressed until it has the shape shown in FIG. 6b. FIGS. 6a and 6b show one possible shape of the bolt, i.e., having a substantially constant diameter over its entire shank, including the forward portion of the shank (except the expandable portion, of course), whereas FIG. 6c shows a bolt having a reduced diameter over the forward portion of the shank.

The shown preferred embodiments are not the only possibilities for realizing the inventive bolt. Some further embodiments are shown in FIGS. 7a and 7b.

Figure 7B:
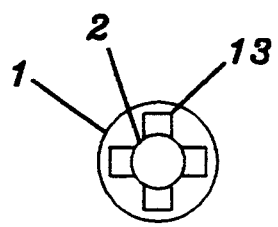
Figure 7A:
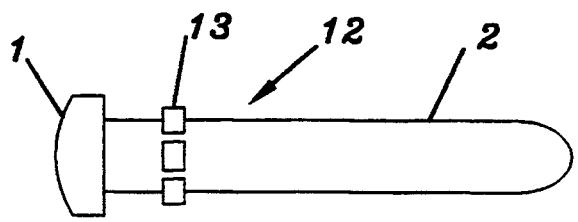

FIGS. 7a and 7b show a bolt having a neck 12 between its head 1 and its shank 2. The neck is provided with a plurality of projections 13 for preventing a rotation of the inserted bolt.

Figure 7D:
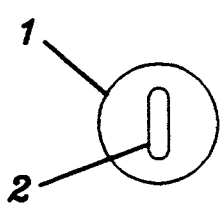
Figure 7C:
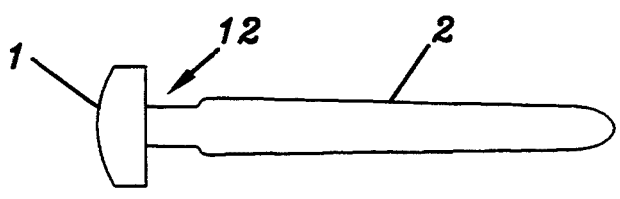

FIGS. 7c and 7d show a bolt having a neck with decreased diameter. This neck helps to retain the bolt in the bone. Furthermore, the shank is gradually tapered towards its tip to make driving the bolt into the bone easier.

FIGS. 8a and 8b show two differing embodiments of the head 1. The head shown in the T-shaped bolt of FIG. 8a is chosen to be long and wide and has a star-shaped profile 15 on the bottom side of the head. A head of this kind can e.g. partially be buried in the bone. The head shown in FIG. 8b has the same diameter as the shank. Therefore, it can be buried more easily in the bone. This head has a recess 4 for receiving the percussion tool as it has been described above.

For hindering a rotation of the bolt, the bottom side of the head can be provided with a profile. Such a profile is especially advantageous when the shank 2 of the bolt has a circular cross section. A bolt with a star shaped profile 15 on the bottom side of its head is shown in FIGS. 9a and 9b. When the bolt is inserted in the bone, this profile can rest on an osteosynthesis plate or an intramedullary nail with a corresponding profile. The two profiles can interlock and provide a rotationally stable connection.

FIGS. 10a 10b show an intramedullary nail with such profiles 16 located around its locking holes or apertures 14. The profiles 16 of the nail are matched to the profile 15 of the bolt and prevent a rotation between the two contacting elements. For this purpose, the bolt must be driven into the bone until the profile 15 on the bottom side of the bolt head contacts the corresponding profile 16 on the top side of the nail. The length of the head should be chosen to correspond at least to the thickness of the hard bone (see also FIGS. 8a and 8c).

In the same manner, an appropriate profile 16 of an intramedullary nail can also cooperate with the projections 13 of a bolt as shown in FIGS. 7a and 7b. In this case, the bolt must be driven into the bone until the projections 13 contact the profile 16 of the nail.

The described bolts can also be coupled to other elements, such as osteosynthesis plates, having the described profiles 16.

The above description shows that the inventive bolt is an element with various applications and embodiments.

While there are shown and described present preferred embodiments of the invention, it is to be distinctly understood that the invention is not limited thereto, but may be otherwise variously embodied and practiced within the scope of the following claims.

We claim:

1. A combination of bone-fixing elements comprising an intramedullary nail having a transverse aperture therein and therethrough and a cooperating locking bolt, said locking bolt having a head portion and shank means for extending into and through said aperture at an angle to said intramedullary nail, said locking bolt comprising means for enlarging a diameter of at least a part of said shank means when said shank means is present in and extends transversely through said aperture, thereby to lock said bolt in said aperture in said intramedullary nail and to lock said intramedullary nail in place in a bone when located therein.

2. The combination of claim 1, wherein said intramedullary nail and said bolt comprise means for preventing rotation of said bolt in said nail.

3. The combination of claim 2, wherein said means for preventing rotation comprises non-rotational symmetric cross-sections of at least a portion of said aperture and of at least a portion of said shank means.

4. A combination of bone-fixing elements comprising an intramedullary nail having an aperture therein and a cooperating locking bolt, said locking bolt having a head portion and a shank for extending into said aperture in said intramedullary nail, said locking bolt comprising means for enlarging a diameter of at least a part of said shank when said shank is present in said aperture, thereby to lock said bolt in said intramedullary nail and to lock said intramedullary nail in place in a bone when located therein, wherein said means for enlarging said diameter comprises a cavity extending through said head portion of said bolt and into said shank, said cavity having a narrowed section and a pin for insertion into said cavity, said pin having a diameter larger than said narrowed section of said cavity so that said narrowed section of said cavity is widened upon insertion of said pin into said cavity.

5. The combination of bone-fixing elements of claim 4, wherein said means for enlarging comprises a jamming member located in a lateral opening of said shank, a portion of said jamming member extending into said cavity for contact with said pin upon insertion of said pin into said cavity and another portion of said jamming member extending outwardly through said opening and into jamming contact with said aperture in said intramedullary nail upon insertion of said pin into said cavity.

6. The combination of claim 4, wherein said means for enlarging comprises longitudinal slots extending over at least a portion of said shank.

7. A combination of bone-fixing elements comprising an intramedullary nail having an aperture therein and a cooperating locking bolt, said locking bolt having a head portion and a shank for extending into said aperture in said intramedullary nail, said locking bolt comprising means for enlarging a diameter of at least a part of said shank when said shank is present in said aperture, thereby to lock said bolt in said intramedullary nail and to lock said intramedullar nail in place in a bone when located therein, wherein said intramedullary nail and said bolt comprise means for preventing rotation of said bolt in said nail, wherein said means for preventing rotation comprises first serrations provided on said intramedullary nail which interlock with second serrations provided on said bolt.

8. A combination of bone-fixing elements comprising an intramedullary nail having an aperture therein and a cooperating locking bolt, said locking bolt having a head portion and a shank for extending into said aperture in said intramedullary nail, said locking bolt comprising means for enlarging a diameter of at least a part of said shank when said shank is present in said aperture, thereby to lock said bolt in said intramedullary nail and to lock said intramedullary nail in place in a bone when located therein, wherein at least a portion of said shank has a non-rotational symmetry.

9. A combination of bone-fixing elements comprising an intramedullary nail having an aperture therein and a cooperating locking bolt, said locking bolt having a shank for extending into said aperture in said intramedullary nail, said nail and said bolt comprising means for preventing rotation of said bolt in said nail, said means comprising first serrations provided on said nail which interlock with second serrations provided on said bolt, thereby to lock said bolt in said intramedullary nail and to lock said intramedullary nail in place in a bone when located therein.

10. The combination of claim 9, wherein said bolt comprises a head which extends outwardly beyond said shank and wherein said second serrations are located at a bottom side of said outwardly-extending head portion.

11. The combination of claim 9, wherein said shank comprises outwardly-extending protrusions forming said second serrations.

* * * * *

UNITED STATES PATENT AND TRADEMARK OFFICE
CERTIFICATE OF CORRECTION

PATENT NO. : 5,387,214
DATED : February 7, 1995
INVENTOR(S) : Philipp R. Kropf, Albert Geisser It is certified that error appears in the above-indentified patent and that said Letters Patent is hereby corrected as shown below:

```
Column  1, line 34; delete the word "and" (Resp. & Amdt.2-17-94)
Column  2, line 33; delete the word "FIG."
Column  2, lines 41-49; delete the lines beginning with
    "a second" and ending with "of the shank"

Column  3, line 27; insert a comma  -- , -- after the letter "c"
Column  5, line 54; "10a 10b" should read  -- 10a and 10b --
```

Signed and Sealed this

Thirtieth Day of May, 1995

Attest:

BRUCE LEHMAN

*Attesting Officer*     *Commissioner of Patents and Trademarks*